United States Patent
Pak et al.

(10) Patent No.: US 11,013,607 B2
(45) Date of Patent: May 25, 2021

(54) TALAR ANKLE IMPLANT

(71) Applicant: ENCORE MEDICAL, L.P., Austin, TX (US)

(72) Inventors: Chulho Pak, Mahwah, NJ (US); Thomas Loring, Philadelphia, PA (US)

(73) Assignee: ENCORE MEDICAL, L.P., Austin, TX (US)

( * ) Notice: Subject to any disclaimer, the term of this patent is extended or adjusted under 35 U.S.C. 154(b) by 146 days.

(21) Appl. No.: 16/137,834

(22) Filed: Sep. 21, 2018

(65) Prior Publication Data
US 2019/0091032 A1    Mar. 28, 2019

Related U.S. Application Data

(60) Provisional application No. 62/562,007, filed on Sep. 22, 2017.

(51) Int. Cl.
*A61F 2/24*    (2006.01)
*A61F 2/42*    (2006.01)
(Continued)

(52) U.S. Cl.
CPC ........ *A61F 2/4202* (2013.01); *A61F 2/30749* (2013.01); *A61F 2/4606* (2013.01); *A61F 2002/30131* (2013.01); *A61F 2002/30159* (2013.01); *A61F 2002/30227* (2013.01); *A61F 2002/30589* (2013.01); *A61F 2002/30604* (2013.01); *A61F 2002/30607* (2013.01); *A61F 2002/30845* (2013.01); *A61F 2002/30879* (2013.01); *A61F 2002/30904* (2013.01); *A61F 2002/4207* (2013.01);
(Continued)

(58) Field of Classification Search
CPC ... A61F 2/42; A61F 2/4202; A61F 2002/4207
See application file for complete search history.

(56) References Cited

U.S. PATENT DOCUMENTS 1,505,106 A    8/1924    Schröder
3,839,742 A    10/1974   Link
(Continued)

FOREIGN PATENT DOCUMENTS

EP    0554959 A1    8/1993
EP    1468652       10/2004
(Continued)

OTHER PUBLICATIONS

Small Bones Innovations, Inc., Star™ Surgical Technique, 2009-2013.
(Continued)

*Primary Examiner* — Jason-Dennis N Stewart
(74) *Attorney, Agent, or Firm* — Veros Legal Solutions LLP

(57) ABSTRACT

The present disclosure includes, in one embodiment, a talar component of an ankle joint prosthesis for engagement with a talus bone having a medial side wall and a lateral side wall, opposite the medial side wall, each side wall terminating at a distal edge, and the distal edges adapted to drive into the talus bone. When implanted, the side walls may form a seal between the talus bone and the component to prevent fluid from flowing under the component.

14 Claims, 5 Drawing Sheets

(51) Int. Cl.
*A61F 2/30* (2006.01)
*A61F 2/46* (2006.01)
(52) U.S. Cl.
CPC ............. A61F 2310/00023 (2013.01); A61F 2310/00179 (2013.01); A61F 2310/00329 (2013.01)

(56) References Cited

U.S. PATENT DOCUMENTS

| | | |
|---|---|---|
| 3,975,778 A | 8/1976 | Newton, III |
| 3,987,500 A | 10/1976 | Schlein |
| 4,021,864 A | 5/1977 | Waugh |
| 4,069,518 A | 1/1978 | Groth, Jr. et al. |
| 4,156,944 A | 6/1979 | Schreiber et al. |
| 4,166,292 A | 9/1979 | Bokros |
| 4,229,839 A | 10/1980 | Schwemmer |
| 4,232,404 A | 11/1980 | Samuelson et al. |
| 4,289,123 A | 9/1981 | Dunn |
| 4,301,552 A | 11/1981 | London |
| 4,499,900 A | 2/1985 | Petrofsky et al. |
| 4,501,269 A | 2/1985 | Bagby |
| 4,524,766 A | 6/1985 | Petersen |
| 4,569,352 A | 2/1986 | Petrofsky et al. |
| 4,570,927 A | 2/1986 | Petrofsky et al. |
| 4,586,495 A | 5/1986 | Petrofsky |
| 4,655,778 A | 4/1987 | Koeneman |
| 4,697,808 A | 10/1987 | Larson et al. |
| 4,711,242 A | 12/1987 | Petrofsky |
| 4,978,357 A * | 12/1990 | Goymann ............... A61F 2/389 623/22.4 |
| 4,990,161 A | 2/1991 | Kampner |
| 5,020,519 A | 6/1991 | Hayes et al. |
| 5,041,139 A | 8/1991 | Brånemark |
| 5,063,937 A | 11/1991 | Ezenwa et al. |
| 5,074,285 A | 12/1991 | Wright |
| 5,122,144 A | 6/1992 | Bert et al. |
| 5,219,364 A | 6/1993 | Lloyd |
| 5,326,365 A | 7/1994 | Alvine |
| 5,336,270 A | 8/1994 | Lloyd |
| 5,344,423 A | 9/1994 | Dietz et al. |
| 5,431,653 A | 7/1995 | Callaway |
| 5,486,180 A | 1/1996 | Dietz et al. |
| 5,514,139 A | 5/1996 | Goldstein et al. |
| 5,571,109 A | 11/1996 | Bertagnoli |
| 5,571,184 A | 11/1996 | DeSatnick |
| 5,630,820 A | 5/1997 | Todd |
| 5,649,929 A | 7/1997 | Callaway |
| 5,662,656 A | 9/1997 | White |
| 5,766,259 A | 6/1998 | Sammarco |
| 5,810,827 A | 9/1998 | Haines et al. |
| 5,824,106 A | 10/1998 | Fournol |
| 5,885,299 A | 3/1999 | Winslow et al. |
| 5,916,216 A | 6/1999 | DeSatnick et al. |
| 5,993,487 A | 11/1999 | Skardoutos et al. |
| 6,053,945 A | 4/2000 | O'Neil et al. |
| 6,090,114 A | 7/2000 | Matsuno et al. |
| 6,099,571 A | 8/2000 | Knapp |
| 6,174,314 B1 | 1/2001 | Waddell |
| 6,183,519 B1 | 2/2001 | Bonnin et al. |
| 6,245,109 B1 | 6/2001 | Mendes et al. |
| 6,284,001 B1 | 9/2001 | Knapp |
| 6,409,767 B1 | 6/2002 | Perice et al. |
| 6,482,236 B2 | 11/2002 | Habecker |
| 6,520,967 B1 | 2/2003 | Cauthen |
| 6,551,316 B1 | 4/2003 | Rinner et al. |
| 6,554,837 B1 | 4/2003 | Hauri et al. |
| 6,610,095 B1 | 8/2003 | Pope et al. |
| 6,663,669 B1 | 12/2003 | Reiley |
| 6,673,116 B2 | 1/2004 | Reiley |
| 6,686,437 B2 | 2/2004 | Buchman et al. |
| 6,699,289 B2 | 3/2004 | Iannotti et al. |
| 6,755,841 B2 | 6/2004 | Fraser et al. |
| 6,852,130 B2 | 2/2005 | Keller et al. |
| 6,860,902 B2 | 3/2005 | Reiley |
| 6,863,691 B2 | 3/2005 | Short et al. |
| 6,866,683 B2 | 3/2005 | Gerbec et al. |
| 6,875,236 B2 | 4/2005 | Reiley |
| 6,887,276 B2 | 5/2005 | Gerbec et al. |
| 6,911,047 B2 | 6/2005 | Rockwood, Jr. et al. |
| 6,926,739 B1 | 8/2005 | O'Connor et al. |
| 6,939,380 B2 | 9/2005 | Guzman |
| 7,011,687 B2 | 3/2006 | Deffenbaugh et al. |
| 7,025,790 B2 | 4/2006 | Parks et al. |
| 7,060,074 B2 | 6/2006 | Rosa et al. |
| 7,118,580 B1 | 10/2006 | Beyersdorff et al. |
| 7,141,053 B2 | 11/2006 | Rosa et al. |
| 7,160,328 B2 | 1/2007 | Rockwood, Jr. et al. |
| 7,204,851 B2 | 4/2007 | Trieu et al. |
| 7,297,165 B1 | 11/2007 | Kriek |
| 7,314,488 B2 | 1/2008 | Reiley |
| 7,323,012 B1 | 1/2008 | Stone et al. |
| 7,361,194 B2 | 4/2008 | Carroll |
| 7,419,491 B2 | 9/2008 | Masini |
| 7,465,303 B2 | 12/2008 | Riccione et al. |
| 7,468,075 B2 | 12/2008 | Lang et al. |
| 7,470,273 B2 | 12/2008 | Dougherty-Shah |
| 7,485,147 B2 | 2/2009 | Pappas et al. |
| 7,491,205 B1 | 2/2009 | Michelson |
| 7,510,557 B1 | 3/2009 | Bonutti |
| 7,534,246 B2 | 5/2009 | Reiley et al. |
| 7,534,270 B2 | 5/2009 | Ball |
| 7,618,451 B2 | 11/2009 | Berez et al. |
| 7,625,409 B2 | 12/2009 | Saltzman et al. |
| 7,628,818 B2 | 12/2009 | Hazebrouck et al. |
| 7,632,279 B2 | 12/2009 | Bastian |
| 7,641,697 B2 | 1/2010 | Reiley |
| 7,717,920 B2 | 5/2010 | Reiley |
| 7,744,601 B2 | 6/2010 | Rosa et al. |
| 7,842,092 B2 | 11/2010 | Otto et al. |
| 7,867,281 B2 | 1/2011 | Carroll |
| 7,914,583 B2 | 3/2011 | Wolfe et al. |
| 7,918,894 B2 | 4/2011 | Wolfe et al. |
| 7,963,996 B2 | 6/2011 | Saltzman et al. |
| 8,002,841 B2 | 8/2011 | Hasselman |
| 8,034,114 B2 | 10/2011 | Reiley |
| 8,048,164 B2 | 11/2011 | Reiley |
| 8,114,091 B2 | 2/2012 | Ratron et al. |
| 8,128,703 B2 | 3/2012 | Hazebrouck et al. |
| 8,241,360 B2 | 8/2012 | Bao et al. |
| 8,267,975 B2 | 9/2012 | McCombs et al. |
| 8,268,007 B2 | 9/2012 | Barsoum et al. |
| 8,277,448 B2 | 10/2012 | Daluiski et al. |
| 8,282,590 B2 | 10/2012 | Goswami et al. |
| 8,313,492 B2 | 11/2012 | Wong et al. |
| 8,388,684 B2 | 3/2013 | Bao et al. |
| 8,403,935 B2 | 3/2013 | Gross |
| 8,430,930 B2 | 4/2013 | Hunt |
| 8,460,304 B2 | 6/2013 | Fitz et al. |
| 8,470,047 B2 | 6/2013 | Hazebrouck et al. |
| 8,480,755 B2 | 7/2013 | Reiley |
| 8,496,712 B2 | 7/2013 | Reiley |
| 8,496,713 B2 | 7/2013 | Bennett et al. |
| 8,545,501 B2 | 10/2013 | Wong et al. |
| 8,556,983 B2 | 10/2013 | Bojarski et al. |
| 8,585,744 B2 | 11/2013 | Duggal et al. |
| 8,597,361 B2 | 12/2013 | Sidebotham et al. |
| 8,617,172 B2 | 12/2013 | Fitz et al. |
| 8,632,600 B2 | 1/2014 | Zannis et al. |
| 8,668,743 B2 | 3/2014 | Perler |
| 8,715,359 B2 | 5/2014 | Deffenbaugh et al. |
| 8,871,142 B2 | 10/2014 | Smith et al. |
| 8,998,991 B2 | 4/2015 | Bennett et al. |
| 9,011,503 B2 | 4/2015 | Duggal et al. |
| 9,101,476 B2 | 8/2015 | Deruntz et al. |
| 9,125,672 B2 | 9/2015 | Fitz et al. |
| 9,144,500 B2 | 9/2015 | Harding, Jr. |
| 9,180,012 B2 | 11/2015 | Jordan et al. |
| 9,204,967 B2 | 12/2015 | Wyss et al. |
| 9,216,085 B2 | 12/2015 | Schwartz et al. |
| 9,237,953 B2 | 1/2016 | Rybolt |
| 9,265,611 B2 | 2/2016 | Schwartz et al. |
| 9,421,108 B2 | 8/2016 | Hunt |
| 9,526,619 B2 | 12/2016 | Schwartz et al. |
| 9,681,955 B2 | 6/2017 | Jordan et al. |

(56) References Cited

U.S. PATENT DOCUMENTS

| | | |
|---|---|---|
| 9,907,561 B2 | 3/2018 | Luna et al. |
| 9,974,588 B2 | 5/2018 | Stemniski et al. |
| 9,993,255 B2 | 6/2018 | McGinley et al. |
| 9,999,516 B2 | 6/2018 | Hunt |
| 10,080,573 B2 | 9/2018 | McGinley et al. |
| 10,106,724 B2 | 10/2018 | Dams et al. |
| 2001/0029377 A1 | 10/2001 | Aebi et al. |
| 2001/0031969 A1 | 10/2001 | Aebi et al. |
| 2002/0116009 A1 | 8/2002 | Fraser et al. |
| 2002/0143343 A1 | 10/2002 | Castro |
| 2003/0212403 A1 | 11/2003 | Swanson |
| 2004/0030399 A1 | 2/2004 | Asencio |
| 2004/0102785 A1 | 5/2004 | Hodorek et al. |
| 2004/0117019 A1 | 6/2004 | Trieu et al. |
| 2004/0122519 A1 | 6/2004 | Wiley et al. |
| 2004/0167631 A1 | 8/2004 | Luchesi et al. |
| 2004/0186585 A1 | 9/2004 | Feiwell |
| 2004/0220582 A1 | 11/2004 | Keller |
| 2004/0249388 A1 | 12/2004 | Michelson |
| 2005/0004676 A1 | 1/2005 | Schon et al. |
| 2005/0027360 A1 | 2/2005 | Webb et al. |
| 2005/0033442 A1 | 2/2005 | Fisher et al. |
| 2005/0049710 A1 | 3/2005 | O'Driscoll et al. |
| 2005/0055028 A1 | 3/2005 | Haines |
| 2005/0113842 A1 | 5/2005 | Bertagnoli et al. |
| 2005/0119665 A1 | 6/2005 | Keller |
| 2005/0165408 A1 | 7/2005 | Puno et al. |
| 2005/0245928 A1 | 11/2005 | Colleran et al. |
| 2005/0288792 A1 | 12/2005 | Landes et al. |
| 2006/0004377 A1 | 1/2006 | Keller |
| 2006/0020345 A1 | 1/2006 | O'Connor et al. |
| 2006/0041311 A1 | 2/2006 | McLeer |
| 2006/0100634 A1 | 5/2006 | Ferguson |
| 2006/0136058 A1 | 6/2006 | Pietrzak |
| 2006/0142870 A1 | 6/2006 | Robinson et al. |
| 2006/0149278 A1 | 7/2006 | Abdou |
| 2006/0195116 A1 | 8/2006 | Fox |
| 2006/0235421 A1 | 10/2006 | Rosa et al. |
| 2006/0241634 A1 | 10/2006 | Tuttle et al. |
| 2006/0247788 A1 | 11/2006 | Ross |
| 2007/0038303 A1 | 2/2007 | Myerson et al. |
| 2007/0088442 A1 | 4/2007 | Cima et al. |
| 2007/0123901 A1 | 5/2007 | Foley et al. |
| 2007/0135924 A1 | 6/2007 | Verhoogen |
| 2007/0173944 A1 | 7/2007 | Keller et al. |
| 2007/0191857 A1 | 8/2007 | Allard et al. |
| 2007/0198025 A1 | 8/2007 | Trieu et al. |
| 2007/0233140 A1 | 10/2007 | Metzger et al. |
| 2008/0015603 A1 | 1/2008 | Collazo |
| 2008/0097617 A1 | 4/2008 | Fellinger et al. |
| 2008/0109081 A1 | 5/2008 | Bao et al. |
| 2008/0167655 A1 | 7/2008 | Wang et al. |
| 2008/0177272 A1 | 7/2008 | Zucherman et al. |
| 2008/0177275 A1 | 7/2008 | Wing et al. |
| 2008/0200988 A1 | 8/2008 | Carroll |
| 2008/0215156 A1 | 9/2008 | Duggal et al. |
| 2008/0269756 A1 | 10/2008 | Tomko et al. |
| 2008/0275452 A1 | 11/2008 | Lang et al. |
| 2008/0306605 A1 | 12/2008 | Hasselman |
| 2008/0312745 A1 | 12/2008 | Keller et al. |
| 2009/0018665 A1 | 1/2009 | Clifford et al. |
| 2009/0030422 A1 | 1/2009 | Parsons et al. |
| 2009/0048603 A1 | 2/2009 | Hoag et al. |
| 2009/0054992 A1 | 2/2009 | Landes et al. |
| 2009/0132047 A1 | 5/2009 | Mansmann et al. |
| 2009/0138021 A1 | 5/2009 | Colquhoun et al. |
| 2009/0182433 A1 | 7/2009 | Reiley et al. |
| 2009/0198341 A1 | 8/2009 | Choi et al. |
| 2009/0234362 A1 | 9/2009 | Blain et al. |
| 2009/0270869 A1 | 10/2009 | Colquhoun et al. |
| 2009/0275951 A1 | 11/2009 | Arcenio et al. |
| 2009/0276052 A1 | 11/2009 | Regala et al. |
| 2009/0306671 A1 | 12/2009 | McCormack et al. |
| 2009/0306675 A1 | 12/2009 | Wong et al. |
| 2009/0306781 A1 | 12/2009 | Kyomoto et al. |
| 2010/0023066 A1 | 1/2010 | Long et al. |
| 2010/0057216 A1 | 3/2010 | Gannoe et al. |
| 2010/0069910 A1 | 3/2010 | Hasselman |
| 2010/0100097 A1 | 4/2010 | Wong et al. |
| 2010/0191244 A1 | 7/2010 | White et al. |
| 2010/0198355 A1 | 8/2010 | Kofoed et al. |
| 2010/0204799 A1 | 8/2010 | Keller et al. |
| 2010/0212138 A1 | 8/2010 | Carroll et al. |
| 2010/0217338 A1 | 8/2010 | Carroll et al. |
| 2010/0318088 A1 | 12/2010 | Warne et al. |
| 2011/0009964 A1 | 1/2011 | Schwartz et al. |
| 2011/0035019 A1 | 2/2011 | Goswami et al. |
| 2011/0112542 A1 | 5/2011 | Gross |
| 2011/0118792 A1 | 5/2011 | Orsak |
| 2011/0125275 A1 | 5/2011 | Lipman et al. |
| 2011/0172780 A1 | 7/2011 | Scheland |
| 2011/0295380 A1 | 12/2011 | Long |
| 2011/0313469 A1 | 12/2011 | McCombs et al. |
| 2011/0313532 A1 | 12/2011 | Hunt |
| 2011/0320005 A1 | 12/2011 | Rydell et al. |
| 2012/0010718 A1 | 1/2012 | Still |
| 2012/0109326 A1 | 5/2012 | Perler |
| 2012/0130434 A1 | 5/2012 | Stemniski |
| 2012/0191210 A1 | 7/2012 | Ratron et al. |
| 2012/0221008 A1 | 8/2012 | Carroll et al. |
| 2012/0245701 A1 | 9/2012 | Zak et al. |
| 2012/0271314 A1 | 10/2012 | Stemniski et al. |
| 2012/0271430 A1 | 10/2012 | Arnett et al. |
| 2013/0030529 A1 | 1/2013 | Hunt |
| 2013/0041473 A1 | 2/2013 | Rouyer et al. |
| 2013/0090739 A1 | 4/2013 | Linares et al. |
| 2013/0103037 A1 | 4/2013 | Wong et al. |
| 2013/0116692 A1 | 5/2013 | Daluiski et al. |
| 2013/0116797 A1 | 5/2013 | Coulange et al. |
| 2013/0123935 A1 | 5/2013 | Hunt et al. |
| 2013/0158672 A1 | 6/2013 | Hunt |
| 2013/0184830 A1 | 7/2013 | Hazebrouck et al. |
| 2013/0197517 A1 | 8/2013 | Gross |
| 2013/0218275 A1 | 8/2013 | Caballes |
| 2013/0325009 A1 | 12/2013 | Duggal et al. |
| 2014/0107794 A1 | 4/2014 | Deffenbaugh et al. |
| 2014/0128985 A1 | 5/2014 | Sanders et al. |
| 2014/0188236 A1 | 7/2014 | McGinley et al. |
| 2014/0207244 A1 | 7/2014 | Sanders et al. |
| 2014/0336658 A1 | 11/2014 | Luna et al. |
| 2014/0350688 A1 | 11/2014 | Michel et al. |
| 2015/0045902 A1 | 2/2015 | Perler |
| 2015/0157339 A1 | 6/2015 | McGinley et al. |
| 2015/0157463 A1 | 6/2015 | Stad et al. |
| 2015/0157467 A1 | 6/2015 | McGinley et al. |
| 2015/0173912 A1 | 6/2015 | Bennett et al. |
| 2015/0282946 A1 | 10/2015 | Hunt |
| 2015/0313715 A1 | 11/2015 | Wainscott et al. |
| 2015/0320567 A1 | 11/2015 | Terrill et al. |
| 2016/0128842 A1* | 5/2016 | Wong .................. A61F 2/30771 623/21.18 |
| 2016/0135957 A1 | 5/2016 | Schwartz et al. |
| 2019/0059918 A1* | 2/2019 | Saltzman ........... A61B 17/1682 |

FOREIGN PATENT DOCUMENTS

| | | |
|---|---|---|
| EP | 2124832 A2 | 12/2009 |
| FR | 2770393 A1 | 5/1999 |
| WO | 1997023172 A2 | 7/1997 |
| WO | 9965403 A1 | 12/1999 |
| WO | 2006052571 A2 | 5/2006 |
| WO | 2007092728 A1 | 8/2007 |
| WO | 2007103826 A2 | 9/2007 |
| WO | 2008076559 A1 | 6/2008 |
| WO | 2008078082 A2 | 7/2008 |
| WO | 2008157415 A1 | 12/2008 |
| WO | 2009015009 A1 | 1/2009 |
| WO | 2009158522 A1 | 12/2009 |

OTHER PUBLICATIONS

Link S.T.A.R. Scandinavian Total Ankle Replacement Brochure; Waldemar Link GmbH & Co.; Hamburg, Germany;1993.

(56) References Cited

OTHER PUBLICATIONS

Link S.T.A.R. Scandinavian Total Ankle Replacement Brochure; Waldemar Link GmbH & Co.; Hamburg, Germany;1990.
StarTM Total Ankle Replacement, Operative Technique, May 2017 Stryker, pp. 1-32.
European Seach Report for Application No. EP18195896 dated Feb. 8, 2019.

* cited by examiner

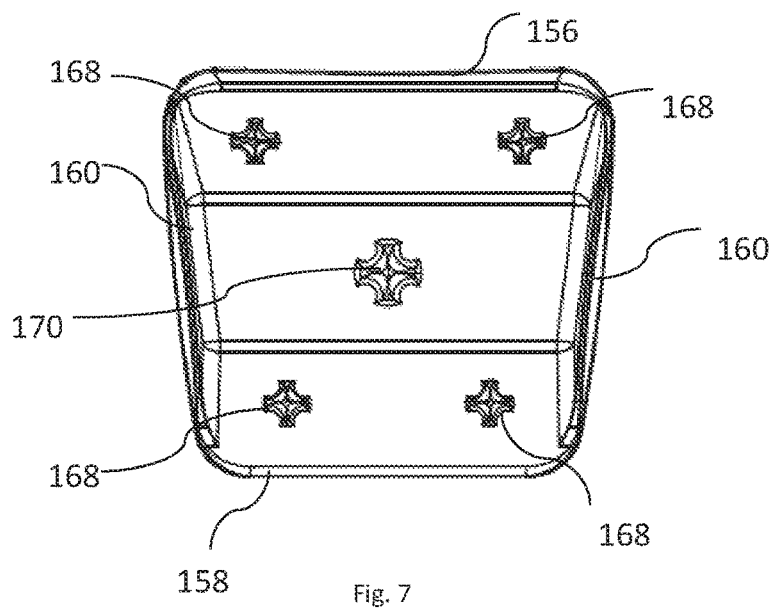
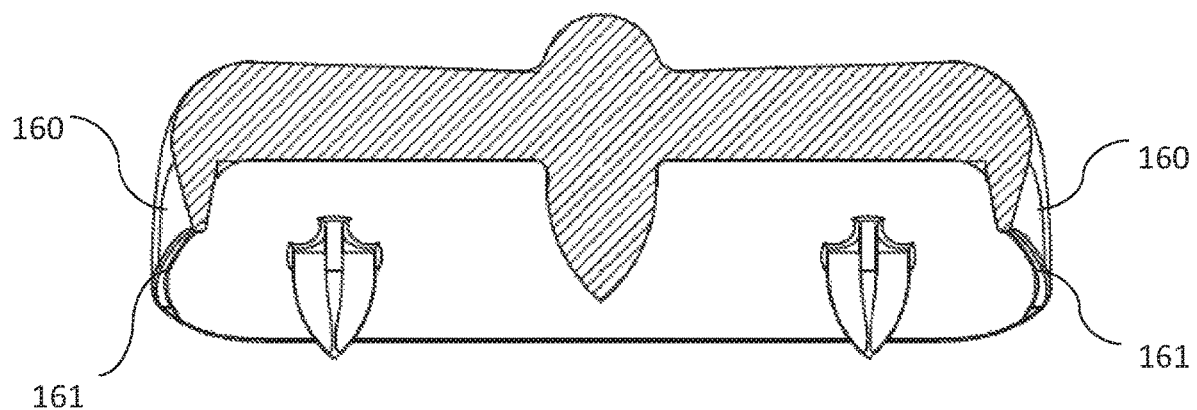

TALAR ANKLE IMPLANT

CROSS-REFERENCE TO RELATED APPLICATIONS

This application claims the benefit of the filing date of U.S. Provisional Application No. 62/562,007, filed Sep. 22, 2017, which is hereby incorporated by reference herein as if fully set forth herein.

BACKGROUND OF THE INVENTION

Ankle pain arises from various conditions including osteoarthritis, post-traumatic arthritis, and rheumatoid arthritis. Generally, a total ankle replacement system, such as S.T.A.R.® or the Scandinavian Total Ankle Replacement System (Howmedica Osteonics, Mahwah, N.J.), includes three components: a first component generally conforming to the talus, a second component generally conforming to the tibia, and a third component being a mobile bearing surface positioned between the first and second components. Such systems may offer a non-cemented implant for replacing a damaged joint while maintaining the range of motion of the ankle.

In certain instances, the talar component of current ankle systems may sit atop the talus, leaving clearance or space between the resected bone and the component. This clearance could reduce fixation of the implant with the bone, and may allow synovial fluid to seep under the implant, which can result in the loosening of the implant. Thus, there is a need in the art for a talar component that increases the chance of achieving a flush fit with the talus regardless of the shape of the talus, the shape of the resected bone surfaces, etc.

BRIEF SUMMARY OF THE INVENTION

The present disclosure relates generally to implants, systems, and methods for ankle repair surgery, including total ankle replacement and partial ankle replacement. In particular, the present disclosure relates to a talar component for use in total or partial ankle repair.

In one embodiment of the present disclosure, a talar component of an ankle joint prosthesis for engagement with a talus bone includes a medial side wall and a lateral side wall, opposite the medial side wall, each side wall terminating at a distal edge, the distal edges adapted to drive into the talus bone.

In other embodiments, the distal edges may be self-cutting edges. The distal edges may be knife-edge, or they may be serrated. With the component implanted in the talus bone, the side walls may form a seal between the talus bone and the component. The talar component may include an inferior surface, in which the inferior surface, medial wall and lateral wall define an inferior volume with the inferior surface positioned facing the talus bone. The seal may enclose a portion of the inferior volume not containing the talus bone, or otherwise a portion of the inferior volume above a surface of the talus bone. The inferior surface may be substantially concave. The talar component may include at least one anchor extending distally from the inferior surface along a longitudinal axis. In one embodiment, the talar component may be symmetrical about an axis extending in the anterior-posterior direction of the component. In an alternate embodiment, one of the medial and lateral side walls may extend farther distally than the other. Each side wall may have a thickness that tapers to form the distal edges. After implantation, for each side wall, substantially the entire length of the distal edge may maintain contact with the talus bone. The seal between the component and the bone may be adapted to prevent fluid from flowing between the inferior surface of the component and the bone.

In another embodiment of the present disclosure, a talar component of an ankle joint prosthesis includes a concave inferior surface adapted to fit on a talus bone and opposing side walls including self-cutting edges, the inferior surface and opposing side walls defining an inferior volume, with the side walls at least partially positioned within the talus bone, the inferior surface and opposing side walls form a seal enclosing a portion of the inferior volume not containing the talus bone (if present) and/or otherwise encloses a volume above a surface of the talus bone situated within the inferior volume.

In other embodiments, for each side wall substantially all of the side wall maintains contact with the talus bone after implantation. A seal between the component and the bone may be formed and be adapted to prevent fluid from flowing between the inferior surface and the bone. Each side wall may have a thickness, the thicknesses tapering to form respective distal edges. One of the side walls may be a medial side wall and the other side wall may be a lateral side wall. One of the medial and lateral side walls may extend farther distally than the other. In an alternate embodiment, the talar component may be symmetrical about an axis extending in the anterior-posterior direction of the component. The talar component may include at least one anchor extending distally from the inferior surface along a longitudinal axis. The distal edges may drive into the bone, thus forming and maintaining the contact with the talus bone, to participate in forming the seal.

In yet another embodiment of the present disclosure, a method of implanting a talar component during ankle surgery includes cutting at least medial and lateral cuts in a talus bone, and driving a self-cutting edge of a lateral side wall of the talar component into the lateral cut and a self-cutting edge of a medial side wall of the talar component into the medial cut.

In other embodiments, the medial and lateral cuts may be oversized such that, during the driving step, the medial and lateral cuts are separated from one another a distance sufficient to provide or preserve portions of the talus bone to be engaged by and to accept the self-cutting edges. During the driving step, at least one anchor extending from the talar component may be driven into the talus bone. After the driving step, the side walls may form a seal between the talus bone and the talar component. The talar component may include an inferior surface such that the inferior surface, medial side wall and lateral side wall define an inferior volume, wherein the seal encloses a portion of the inferior volume not containing the talus bone (if present) and/or otherwise encloses a volume above a surface of the talus bone situated within the inferior volume.

BRIEF DESCRIPTION OF THE DRAWINGS

FIG. 7 is a bottom view of the talar component of FIG. 3;

FIG. 8 is a cross-sectional view of the talar component of FIG. 3, viewed from the posterior end.

DETAILED DESCRIPTION

In the present disclosure, the term "proximal" generally means closer to the heart and the term "distal" generally means farther away from the heart. The term "posterior" means a position towards the rear of the body and the term "anterior" means a position toward the front of the body. The term "superior" means a position closer to the head and the term "inferior" means a position closer to the feet.

Figure 1:
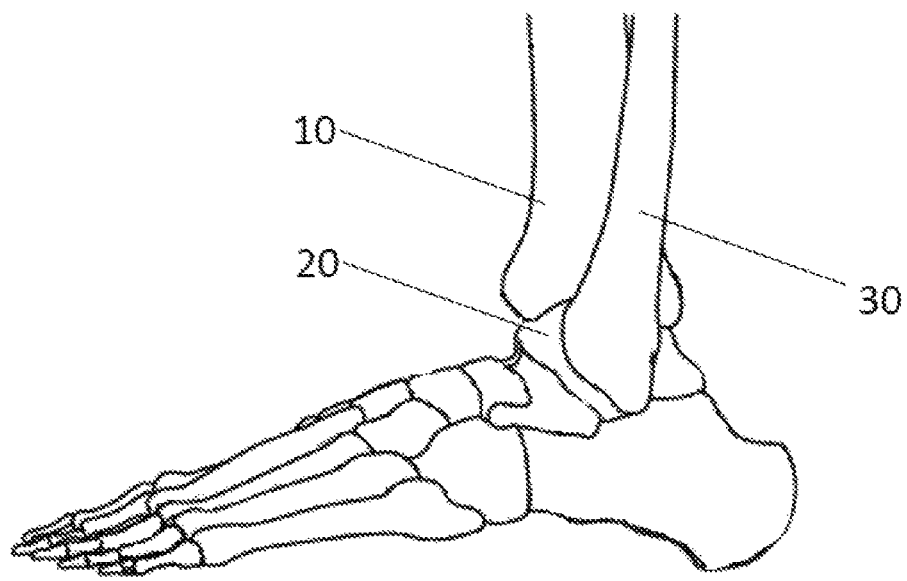
FIG. 1 is a side view of bones of the foot and ankle.
Figure 2:
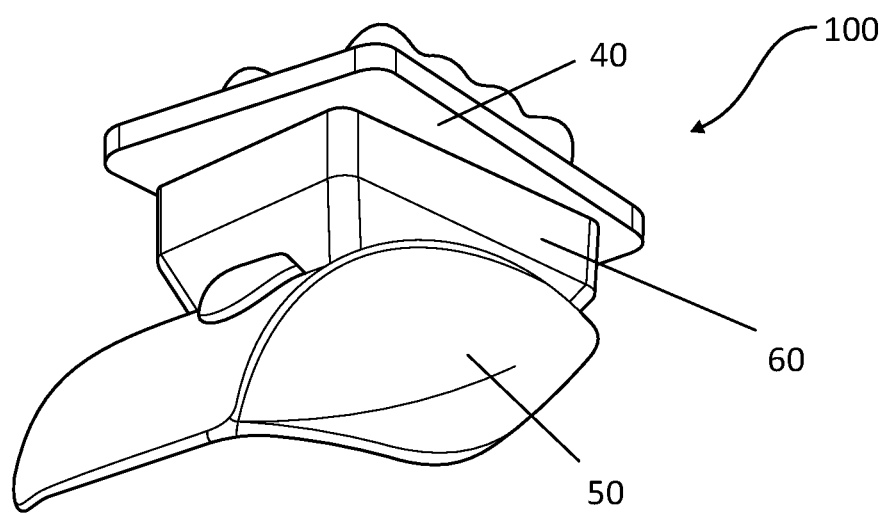
FIG. 2 is a perspective view of components of an ankle joint prosthesis.
Figure 3:
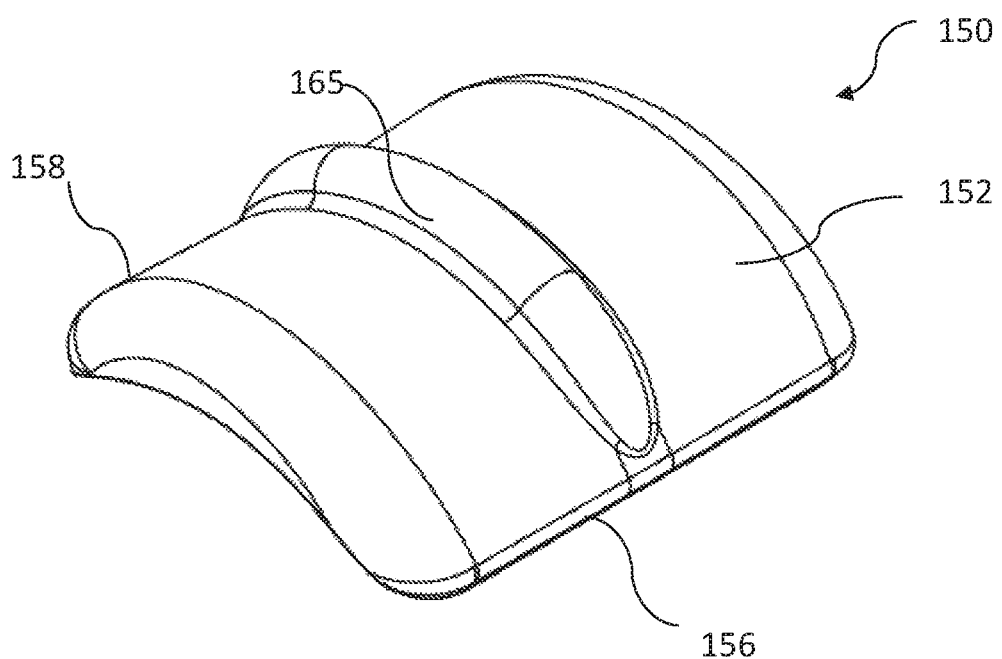
FIG. 3 is a perspective side view of a talar component of an ankle joint prosthesis according to an embodiment of the present disclosure.

FIG. 1 illustrates a simplified side view of the bones of the foot and ankle, including the distal tibia 10, the talus 20, and the distal fibula 30. In one example, the distal tibia 10 and the proximal talus 20 may be arthritic and need replacing with a partial or full joint replacement implant. FIG. 2 illustrates an example of a full joint replacement implant 100 including a tibial component 40, a talar component 50, and a mobile bearing 60 (e.g., typically formed of ultra-high molecular weight polyethylene or other plastic) interposed between the tibial and talar components (e.g., typically formed of metal or the like).

Figure 4:
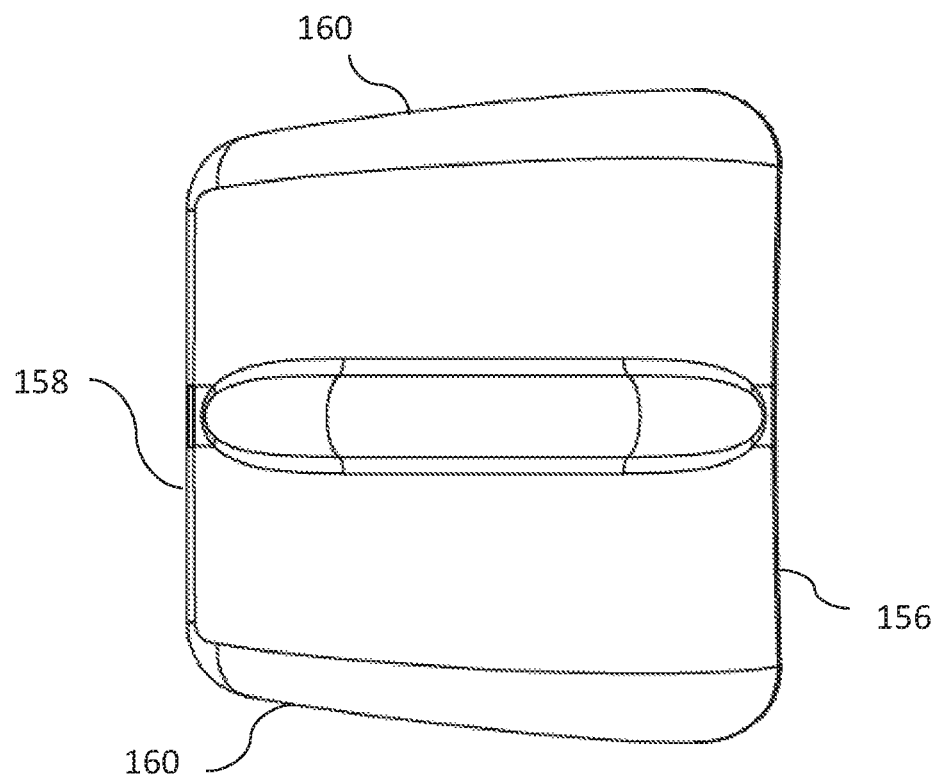
FIG. 4 is a top view of the talar component of FIG. 3.

The present disclosure includes a talar component which may be used as a partial joint replacement implant or as part of a total replacement ankle implant. FIGS. 3-9 show one embodiment of such a talar component 150 for use in a total replacement ankle implant such as implant 100. Talar component 150 includes superior and inferior surfaces 152, 154 respectively, anterior and posterior edges 156, 158, respectively, and opposing medial and lateral side walls 160 extending at least partially between the anterior and posterior edges. From the top view, as shown in FIG. 4, talar component 150 may taper outwardly from posterior edge 158 to anterior edge 156, such that the distance between side walls 160 is greater nearer to the anterior edge than the posterior edge. However, as is commonly known in the art, the particular shape of component 150 may be different depending on particular sizes of the implant, such as implants of an intended size for a particular anatomy of a particular patient, and the like. In any event, the shape of talar component 150 is designed to cover the talar dome and the medial and lateral facets of the ankle as well as provide for a full range of motion in at least the anterior and posterior directions.

Continuing with the illustrated embodiment of FIGS. 3-9, the superior surface 152 of component 150 forms the articulation surface and has a shape complementary to the curvature of the other components of the full joint replacement implant, such as the bearing component, and in the illustrated embodiment, the superior surface is generally convex. A raised ridge 165 may optionally be positioned on the superior surface 152 and may project proximally from superior surface 152. Ridge 165 may extend in the anterior-posterior direction on the superior surface. Ridge 165 may be positioned anywhere on the superior surface as desired, such as substantially in the medial-lateral center of the superior surface and may further have a generally curved shape. If present, ridge 165 is designed to help constrain the motion of the bearing component in the medial-lateral direction. For example, during plantar flexion (e.g., flexion) or dorsiflexion (e.g., extension) of the ankle implant, ridge 165 would track within a complementary channel in the bearing component.

Continuing with this embodiment of FIGS. 3-9, inferior surface 154 is generally concave to conform to the talar dome of the natural ankle, and the adjacent side walls 160 defines an inferior volume. In this manner, the talar component is designed to minimize the amount of bone removal during surgery. Thus, while the inferior surface is designed to comport with the talar dome as closely as possible, since every anatomy is slightly different, the inferior surface 154 may not conform exactly to the talar dome, which may result in volume(s) of open space between the implant and the bone within the defined inferior volume.

Figure 5:
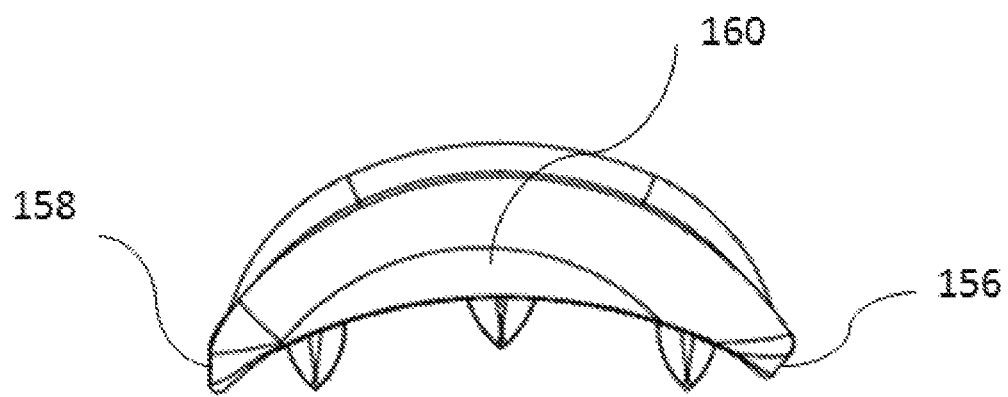
FIG. 5 is a side view of the talar component of FIG. 3.
Figure 6:
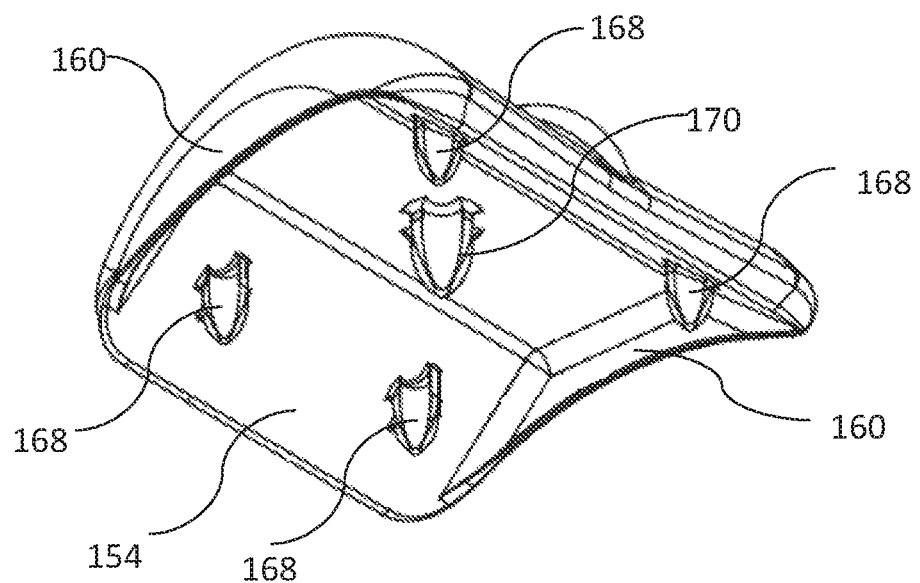
FIG. 6 is a perspective bottom view of the talar component of FIG. 3.

As shown in FIGS. 5 and 6, talar component 150 may also include at least one anchor 168, 170 extending distally from inferior surface 154 to a distal tip. In the illustrated embodiment, two anchors 168 are positioned spaced apart near anterior edge 156, two anchors 168 are positioned spaced apart near posterior edge 158, and one anchor 170 is positioned substantially centrally on the inferior surface 154. This positioning of the anchors is substantially symmetrical in the lateral-medial direction, which may help to minimize rocking or tilting of the talar component relative to the talus 20. In the illustrated embodiment, anchor 170 is larger in size than anchors 168; however, in other embodiments, the anchors may be any size relative to each other. For example, anchor 170 may be the same size or smaller than anchors 168, and anchors 168 may all be different sizes relative to each other. Anchors 168, 170 aid in the fixation of talar component 150 to the bone, and may particularly assist in initial fixation. In alternative embodiments, talar component 150 may include more or less anchors arranged in a variety of positions on the inferior surface 154, and may not include any anchors. Further, while the illustrated anchors 168, 170 are star-shaped, each anchor may have any shape desired. Still further, while the illustrated anchors extend along axes that are generally parallel to one another and perpendicular to the component 150 body, each anchor may extend in any direction relative to the component body and/or one another as desired.

Figure 9:
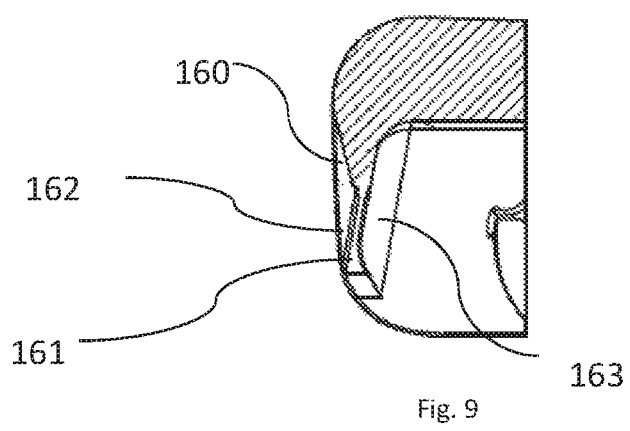
FIG. 9 is a cross-sectional view of a side wall of the talar component of FIG. 3, viewed from the anterior end.

Continuing with the illustrated embodiment, side walls 160 extend to and terminate at distal bone-cutting edges 161. As best shown in FIGS. 8-9, each side wall 160 has a thickness, measured from outer surface 162 to inner surface 163 of the side walls, the thickness tapering to form bone-cutting edges 161. Bone-cutting edges 161 may have a sharpness capable of driving into bone, e.g., functioning as self-cutting edges. Edges 161 may be any type of edge that enables the edge to cut or drive into the bone, e.g. knife-edge, serrated, etc.

Edges 161 and side walls 160 may drive into the bone to provide a flush fit with the talus with substantially little to no clearance or space between side walls 160 and the talus. The bone contacted by edges 161 may be the natural talus or could be the prepared cut surfaces of the talus, as discussed below. The fit is flush such that substantially all of side walls 160 (e.g., along length of side walls 160) of talar component 150 maintains contact with the talus after implantation which may form a seal to prevent synovial fluid from flowing under talar component 150 into any volume of open space which may be present between the bone and inferior surface 154 due to differences between the shape of the inferior surface 154 and the talus 20, as discussed above. The prevention of synovial fluid from seeping under the implant may provide greater fixation of the implant to the bone and increases the longevity of the implant within the patient. Further, the fit between edges 161 and the bone 20 may supplement fixation by anchors 168, 170, or in some instances, could be sufficiently secure such that anchors 168, 170 need not be present on the component 150.

The fit between edges 161 and bone 20 may be particularly strong in instances where bone-cutting edges 161 could facilitate osteointegration between the talar component 150 and the bone. The anchorage of the talar component 150, and in particular the anchorage of edges 161, may enable the formation of bony tissue around the component to provide greater structural and functional connection between the component and the bone.

In another embodiment, one or both of side walls 160 may extend further distally than in the illustrated embodiment. In such a case, one or both of the bone-cutting edges 161 may be positioned further distally, relative to the inferior surface 154 of the talar component 150 such that the edges 161 may extend deeper into the talus 20 which may provide for increased fixation and increased surface area for potential osteointegration, as discussed further below.

In yet another embodiment, talar component 150 may also include sharp bone-cutting edges on anterior and posterior edges 156, 158 (or, such cutting surface could be in place of edges 161, whereby medial/lateral walls 160 do not include cutting edges). In instances where all four sides 156, 158, 160 include cutting edges, such a talar component may have still further engagement ability with the talus to provide for improved sealing of any volume of open space between the inferior surface 154 and the bone 20, and further, could result in osteointegration around the perimeter of the component 150.

Talar component 150 may be comprised of metal, such as titanium, ceramic, glass, polymer, or any other material known for use in the human body. The component 150 may also comprise one or more surface treatments, on any or all of inferior surface 154, edges 156, 158 and side walls 160, to encourage biological fixation, such as porous coating, plasma spray coating, e.g. titanium plasma spray coating, hydroxyapatite, or tricalcium phosphate.

The present disclosure also includes a method of implanting talar component 150 on a prepared talus. In one embodiment, the method generally includes cutting at least medial and lateral cuts on talus 20 to form a prepared talus, digging a bone-cutting edge 161 of a side wall 160 into one of the medial and lateral cuts and digging the second bone-cutting edge 161 of the second side wall into the other of the medial and lateral cuts. The medial and lateral cuts may be oversized to provide greater space for the bone-cutting edges to dig into the cut to form a seal between the side walls and the bone. In other words, such cuts would typically be insufficient to allow space for medial/lateral side walls of an implant to be positioned on the bone, but side walls 160 of component 150, with cutting edges 161, are able to dig into the remaining cut surfaces of the bone to help provide a secure and complete connection between the side walls 160 and the bone 20 along the lengths of the side walls 160. If present, upon pressing component 150 onto the prepared talus, anchors 168, 170 would also be forced into the talus 20 to provide added fixation of the component 150 to the talus. Further, while anchors 168, 170 may be self-tapping, the operator may prepare the talus as desired by decortication of the talus, preparation of pilot holes or bone holes for accepting the anchors, or the like.

The present disclosure may also include various systems and kits based on the components discussed above. While it is envisioned that these various components may be utilized, packaged, sold, or designed in any number of systems and kits, representative embodiments will be discussed in detail below.

The present disclosure can include a kit which can be packaged in a single package as a system or in multiple packages that can be selected as needed by the operator to form a system. For example, such a kit may include at least one talar component 150, at least one tibial component, such as tibial component 40, and at least one mobile bearing, such as bearing 60. Any combination of components including the talar component may be included in a single package or in separate packaging which are later brought together as a kit. If multiple components of any of the specific components are present, such components may differ in size, material, configuration, and the like, such that the operator can select a particular component from a variety of available components depending on need based on surrounding anatomy, bone size, bone density, and the like. Any such kit may also include a surgical procedure which may include instructions or protocol for using the components and may include aspects of any of the above-discussed embodiments, though other variations are also envisioned within the scope of the present disclosure.

In another embodiment, the present disclosure includes a system for the repair of an ankle including at least one talar component, at least one mobile bearing, and at least one tibial component, and a surgical procedure. The surgical procedure may include instructions or protocol for using the components and may include aspects of any of the above-discussed embodiments, though other variations are also envisioned within the scope of the present disclosure.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A talar component of an ankle joint prosthesis for engagement with a talus bone, comprising a medial side wall and a lateral side wall, opposite the medial side wall, each side wall terminating at a distal edge, wherein the distal edges are adapted to drive into the talus bone; and wherein each side wall has a thickness, the thicknesses tapering to form the distal edges.

2. The talar component of claim 1, wherein the distal edges are self- cutting edges.

3. The talar component of claim 1, wherein the distal edges are knife- edge.

4. The talar component of claim 1, wherein the distal edges are serrated.

5. The talar component of claim 1, wherein, with the component engaged with the talus bone, the side walls are configured to form a seal between the talus bone and the component.

6. The talar component of claim 5, further comprising an inferior surface, the inferior surface, medial wall and lateral wall defining an inferior volume, the inferior surface positioned facing the talus bone.

7. The talar component of claim 6, wherein the seal encloses a portion of the inferior volume above a surface of the talus bone.

8. The talar component of claim 6, wherein the inferior surface is substantially concave.

9. The talar component of claim 6, further comprising at least one anchor extending distally from the inferior surface along a longitudinal axis.

10. The talar component of claim 1, wherein the talar component is symmetrical about an axis extending in the anterior-posterior direction of the component.

11. The talar component of claim 1, wherein one of the medial and lateral side walls extends farther distally than the other.

12. A talar component of an ankle joint prosthesis comprising:
   a concave inferior surface adapted to fit on a talus bone; and
   opposing side walls extending distally from the inferior surface, the opposing side walls including self-cutting edges, wherein the inferior surface and opposing side walls define an inferior volume and, with the side walls positioned within the talus bone, the inferior surface and opposing side walls are configured to form a seal enclosing a portion of the inferior volume above a surface of the talus bone; and wherein each side wall has a thickness, the thicknesses tapering to form the distal edges.

13. The talar component of claim 12, wherein for each side wall substantially an entire length of the side wall maintains contact with the talus bone after implantation.

14. The talar component of claim 12, wherein the seal between the component and the bone is adapted to prevent fluid from flowing between the inferior surface and the bone.

* * * * *